United States Patent

Zhou et al.

[11] Patent Number: 6,048,496
[45] Date of Patent: Apr. 11, 2000

[54] MIXER FOR LIQUID CHROMATOGRAPH

[75] Inventors: Xiaojing Zhou, Iruma; Yoshihiko Takano, Iruma, both of Japan

[73] Assignee: GI Sciences Incorporated, Tokyo, Japan

[21] Appl. No.: 08/869,773

[22] Filed: Jun. 5, 1997

[30] Foreign Application Priority Data

Jun. 5, 1996 [JP] Japan .................................. 8-143032

[51] Int. Cl.[7] .................................................. G01N 30/34
[52] U.S. Cl. ........................ 422/70; 73/61.56; 210/198.2; 366/273; 366/338; 422/99
[58] Field of Search ................... 422/70, 99; 436/161; 310/198.2, 656; 73/61.56; 366/273, 274, 336, 338

[56] References Cited

U.S. PATENT DOCUMENTS

| | | |
|---|---|---|
| 3,276,751 | 10/1966 | Svensson et al. . |
| 3,830,369 | 8/1974 | Pfadenhauer . |
| 3,905,395 | 9/1975 | Hupe . |
| 4,496,245 | 1/1985 | Conrad . |
| 4,506,987 | 3/1985 | Daughton et al. . |
| 5,656,034 | 8/1997 | Kochersperger et al. . |
| 5,664,938 | 9/1997 | Yang . |

FOREIGN PATENT DOCUMENTS

| | | |
|---|---|---|
| 3-277966 | 12/1991 | Japan . |
| 3-282362 | 12/1991 | Japan . |
| 5-223803 | 9/1993 | Japan . |
| 6-324028 | 11/1994 | Japan . |
| 7-6759 | 1/1995 | Japan . |

Primary Examiner—Jan Ludlow
Attorney, Agent, or Firm—Wenderoth, Lind & Ponack, L.L.P.

[57] ABSTRACT

A mixer for a liquid chromatograph mixes plural kinds of liquids. It has a first mixer 45 for forcibly agitating the liquids and a second mixer 58 for agitating the liquids in accordance with a flow rate. Liquid passages of the first and second mixers 45, 58 are in communication with each other, and the first and second mixers 45, 58 are integrally mounted.

6 Claims, 8 Drawing Sheets

RESULT OF ANALYSIS USING THE MIXER
ACCORDING TO THE PRESENT INVENTION

FIG. 8

RESULT OF ANALYSIS USING THE CONVENTIONAL MIXER

MIXER FOR LIQUID CHROMATOGRAPH

FIELD OF THE INVENTION

This invention relates to a mixer for a liquid chromatograph, and more particularly to a gradient mixer, for example, suited to be used a liquid chromatograph, which is capable of correctly following a gradient program, in which a sufficient mixing effect, as well as an enhancement of the mixing efficiency, can be obtained, and in addition the liquid chromatograph to be designed small in size and light in weight.

DESCRIPTION OF THE PRIOR ART

A gradient elution method according to a liquid chromatograph is a method for analysis of a sample containing a plurality of ingredients, in which elution is performed by linearly, exponentially or stepwise gradually changing characteristics such as the kinds of mobile phase solvents, condensation of salt, pH, and the like from a weak solvent strength to a stronger solvent strength.

Use of this method makes it possible to obtain suitable separation elution conditions even when a large number of ingredients are to be analyzed. Also, while ensuring separation of the peak of ingredients which are eluted rapidly, spread of the peak of ingredients which elute slowly is suppressed, thereby enhancing the sensitivity of detection.

Gradient mixers are used for mixing mobile phase solvents. With respect to the gradient mixers, there is known a type in which beads are filled in a coil or a mixing chamber. There are also known a static mixer and a dynamic mixer, as disclosed in Japanese Laid-Open Utility Model Publication No. 6759/1996, the former being designed such that dead volume is disposed in a mixing chamber and a plurality of solvents are almost forcibly agitated, while the latter is designed such that a plurality of solvents are forcibly agitated.

Among those conventional gradient mixers, the coil-like static mixer requires a predetermined length dimension sufficient to obtain a sufficient mixing result and is, therefore, readily subject to external conditions such as the installation space, the arrangement, etc. On the other hand, the dynamic mixer has problems such that concentration of ingredients in a direction of flow of the solvents is lessened to zero and therefore, the ingredients are degraded in accuracy and also in reproduction. In addition, no satisfactory result of analysis can be obtained because the replacement reaction is slow.

Although the conventional liquid chromatograph mixers are easy to perform a mixing operation because the dead volume is generally large, it has a problem is being unable to correctly follow the gradient program because mixing ratios of the solvents, which vary with the passage of time are made uniform. This problem is particularly serious when the flow rate is slow.

Moreover, a long time is required for the solvent to return to its initial composition and for the column to return to its initial state, and a reproduction of analysis is inferior.

On the other hand, if the dead volume is small, there are problems such that no sufficient mixing effect can be obtained, and noise is increased so as to make a reproduction of analysis extremely bad. Especially, in case the mixing ratio is abruptly changed, an imperfect mixing results and the physical property of the mobile phase is non-uniform in a vertical section in a direction of movement, thus resulting in an adverse effect on the separation of the ingredients to be analyzed and the result of analysis.

Therefore, it is demanded that gradient mixers can correctly follow the gradient program and that a sufficient mixing effect can be obtained.

On the other hand, the conventional mixers are encumbered with problems such that they are readily adversely affected by pulsation of a liquid feed pump, and noises are likely to occur. As a consequence, the accuracy of analysis is sacrificed.

In this case, if any buffer means such as a coil suitable for absorbing the pulsation should be provided, followability to the gradient program would be degraded because a flow passage of the solvent is increased in volume to that extent. Moreover, the form of the peak of the chromatograph would be spread and a large sized design and heavy weight of the liquid chromatograph result.

SUMMARY OF THE INVENTION

It is, therefore, an object of the present invention to provide a mixer for liquid chromatograph in which a sufficient mixing effect, as well as enhancement of the mixing efficiency, can be obtained.

Another object of the present invention is to provide a mixer for a liquid chromatograph capable of correctly following a gradient program.

A further object of the present invention is to provide a mixer for liquid chromatograph in which the number of parts can be reduced and the chromatograph can be made small in size and light in weight.

A still further object of the present invention is to provide a mixer for a liquid chromatograph suited to be used as a gradient mixer for a liquid chromatograph.

A yet further object of the present invention is to provide a mixer for a liquid chromatograph which can be used not only as a dynamic mixer but also as a static mixer.

A mixer for a liquid chromatograph for mixing plural kinds of liquids comprises a first mixer for forcibly agitating liquid, a second mixer for agitating liquid in accordance with a flow rate, and a liquid passage for the first mixer and a liquid passage for the second mixer in communication with each other, the first and second mixers being integrally mounted.

Owing to the above construction, a sufficient mixing effect, as well as enhancement of mixing efficiency, can be obtained, and in addition, the number of parts can be reduced and a small-sized design and a light weight can be obtained.

BRIEF DESCRIPTION OF THE DRAWINGS

The above objects, features and advantages of the present invention will become manifest from the following detailed description with reference to the accompanying drawings.

DETAILED DESCRIPTION OF PREFERRED EMBODIMENTS

Figure 1:
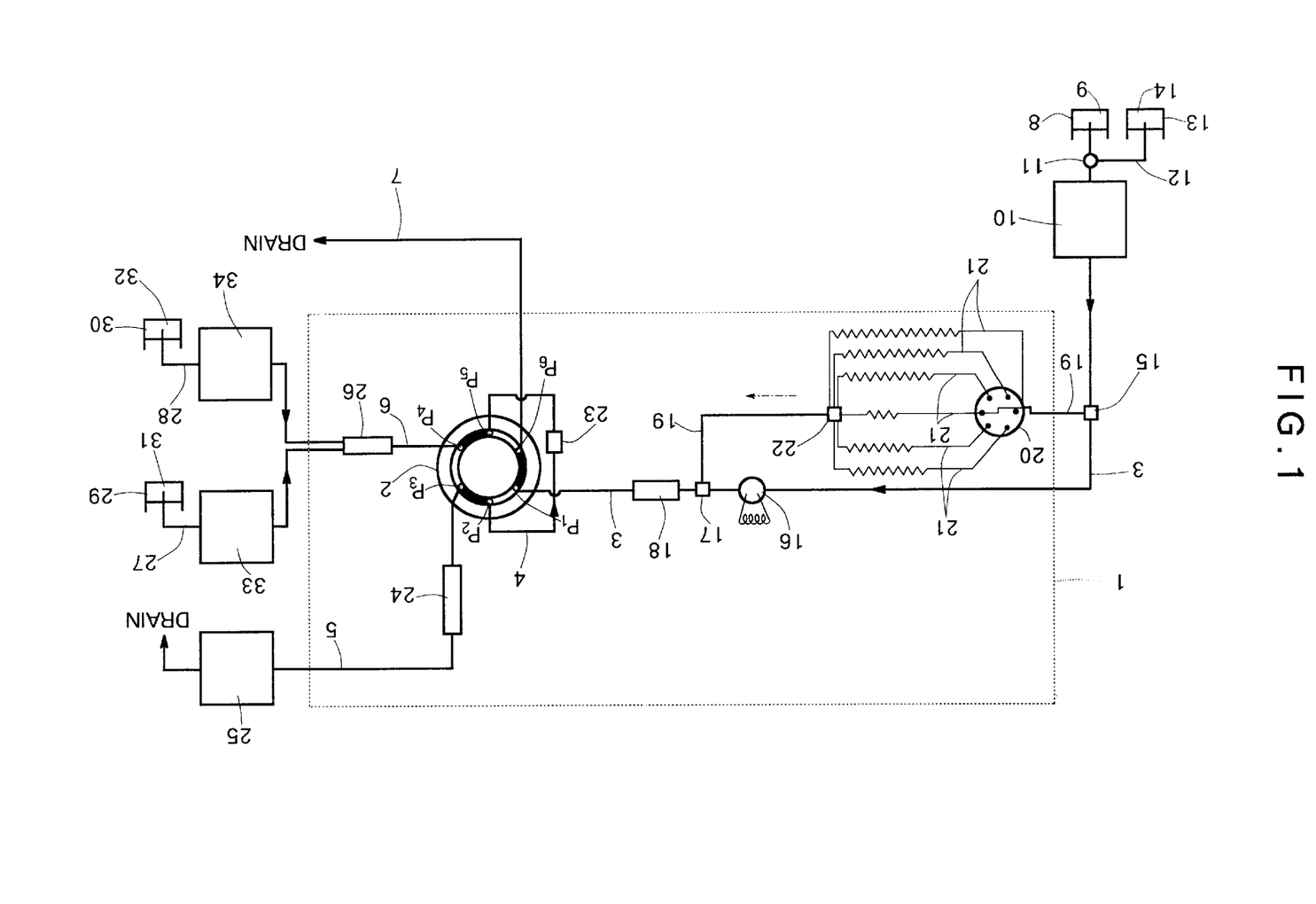
FIG. 1 is an explanatory view of an analytical system showing one embodiment of the present invention.

The present invention will now be described in a form of one preferred embodiment as illustrated, in which the present invention is applied to a gradient mixer for a liquid chromatograph. FIG. 1 shows an analytical system for aldehydes contained in exhaust gas from automobiles. In the Figure, reference numeral 1 denotes a column oven of a liquid chromatograph. A rotary control type six port valve 2 for column switching is disposed within the oven 1. The six port valve 2 includes six ports P1 through P6 which are in communication with the outside. One end of a dilution tube 3 is connected to the port P1, opposite ends of a condensation tube 4 are connected to the ports P2, P5, one end of an analytical tube 5 is connected to the port P3, one end of a mixing tube 6 is connected to the port P4, and one end of a discharge tube 7 is connected to the Port P6.

The other end of the dilution tube 3 is in communication with a dilution liquid 9 such as water contained in a dilution liquid container 8. A liquid feed tank 10 for the dilution liquid 9 is connected to the tube 3 on its upstream side. A switch valve 11 is interposed between the dilution liquid container 8 and the liquid feed pump 10. One end of a cleaning tube 12 is connected to the switch valve 11, and the other end of the cleaning tube 12 is in communication with a cleaning fluid 14 received in a cleaning fluid container 13.

A three port valve 15 is connected to the dilution tube 3 on the downstream side of the liquid feed pump 10, an injector 16 for injecting a sample containing DNPH (2,4-dinitrophenyhydrazine) aldehydes is connected to the three port valve 15 on its downstream side, and a mixer 18 is connected to the injector 16 on its downstream side through a three port valve 17. The mixer 18 used in this embodiment is a second mixer as later described.

A bypass tube 19 is connected between the three port valves 15 and 17. A resistor setter 20 is connected to the bypass tube 19 on its upstream side and first ends of a plurality of resistor tubes 21 having various passage resistance values are connected to the resistor setter 20 so that the resistor tubes 21 can selectively be switched.

[The other end of each resistor tube 21 is connected to a joint 22 which is provided with seven ports, and the bypass tube 19 is connected to the joint 22.

A condensation column 23 is connected to the condensation tube 4, the other end of the analytical tube 5 is in communication with a drain, an analytical column 24 is connected to the analytical tube 5, and a detector 25 is disposed in the analytical column on its downstream side.

A mixer 26 is connected to the other end of the mixing tube 6, and downstream side end portions of a plurality of elute conduits 27, 28 are connected to the mixer 26. Upstream side end portions of the elute conduits 27, 28 are in communication with various kinds of elutes 31, 32 contained in elute containers 29, 30.

[In this embodiment, 10% of THF (tetrahydrofuran) is used as the elute 31, and CH3CN (acetonitrile) is used as the elute 32. They can be supplied to the mixer 26 through the liquid feed pumps 33, 34.

[The liquid feed pumps 33, 34 are controllable in discharge quantity based on various conditions for analysis and in accordance with a gradient program, thereby enabling the formation of a predetermined mixing ratio for the elutes 31, 32.

The elute conduits 27, 28 are preferably provided on their downstream side end portions or connection ports 35a, 35b with a check valve for preventing a back-flow of the elutes 31, 32.

Figure 2:
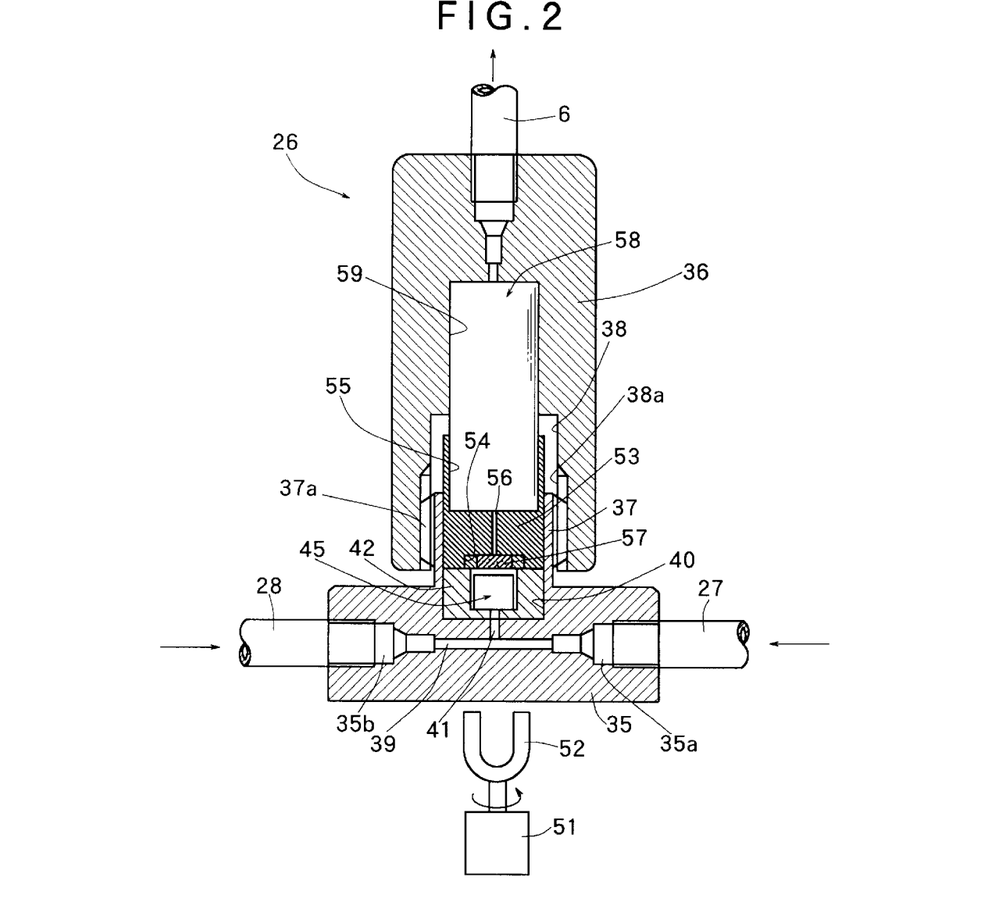
FIG. 2 is a sectional view showing the one embodiment of the present invention.

As shown in FIG. 2, the mixer 26 includes a three-way joint 35 into which end portions of the elute tubes 27, 28 can be screwed, and a sleeve-like cap 36 into which a downstream side end portion of the mixing tube 6 can be screwed. They are integrally joined by screwing an outlet tube 37 of the three-way joint 35 into a joint hole 38 of the cap 36.

In the illustration, reference numeral 37a denotes a threaded portion formed in a peripheral surface of the end of the outlet tube 37, and 38a, a threaded portion formed in an inner surface of the joint hole 38.

Within the three-way joint 35, an inlet port 39 is provided. The inlet port 39 is in communication with connection ports 35a, 35b of the elute conduits 27, 28. Within the outlet tube 37, a concave chamber 40 having an enlarged diameter is defined. An outlet port 41 in communication with the inlet port 39 is opened at a bottom portion of the concave chamber 40.

A spacer 42 is received in the bottom portion of the concave chamber 40, a recess 43 is formed in an axial direction of the spacer 42, and a passage 44 in communication with the outlet port 41 is formed in a bottom portion of the recess 43. A first mixer 45 of a dynamic type is received in the recess 43.

The first mixer 45 includes a housing 46 for dividing outside. A mixing chamber 47 having a small volume is defined within the housing 46. An inlet/outlet port of the mixing chamber 47 is tapered so that a dead space of the inlet/outlet port is reduced.

Through-holes 48, 49 in communication with the mixing chamber 47 are disposed at opposing locations of the housing 46. The through-hole 49 is in communication with the recess 43.

In this case, the housing 46 may be eliminated and an agitator as later described may be received directly in the recess 43. By doing so, a dead volume caused by the housing 46 is reduced and the number of parts is reduced, too. At that time, the recess 43 is preferably made as compact in volume as the mixing chamber 47 and slightly reduced in diameter on both its upstream and downstream sides so that the dead volume may be reduced.

Figure 3:
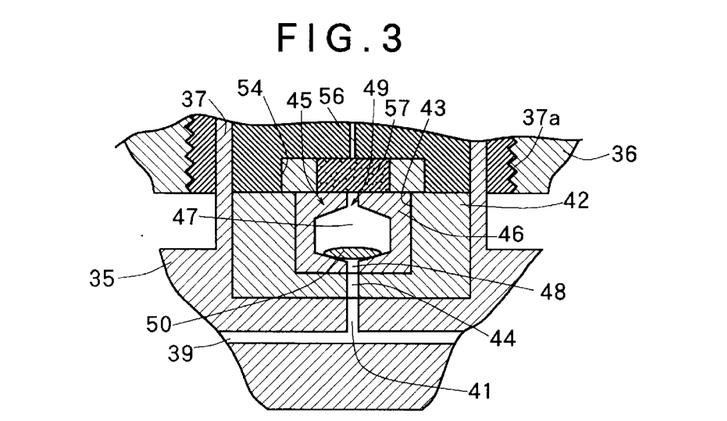
FIG. 3 is a partly enlarged view, showing one embodiment of a first mixer which is applied to the present invention.

An agitator 50 made of a magnet coated with Teflon (merchandise name manufactured by Du Pont) is rotatably received in the mixing chamber 47. The agitator 50 is formed in the shape of a stone as is used in a Go game (Japanese chess), as shown in FIG. 3, or in the shape of a ball as used in rugby football, or in the shape of a circular sleeve. The agitator 50 is normally located on an inner opening portion of the through-hole 48.

In the illustration, reference numeral 51 denotes an agitation motor installed immediately under the three-way joint 35. The motor 51 is variable in speed of rotation within a range of from 0 to 500 rpm. An output shaft of the motor 51 is provided with a rotor 52 made of a magnet and having a generally U-shaped configuration. Owing to this arrangement, the agitator 50 is drawn by magnetic force of the rotor 52 such that the agitator 50 can be rotated in synchronism with the rotor 52.

A mixer base 53 is received on the spacer 42. The mixer base 53 is provided at axially opposite end portions thereof with recesses 54, 55. They are in communication with each other through an introduction hole 56.

The recess 54 is disposed opposite the recess 43, and a filter 57 is attached to the recess 54. The recess 55 is in communication with the joint hole 38. One end of a second mixer 58 of a static mixer type is received in the recess 55 and the other end is inserted into a fitting hole formed in an inner part of the joint hole 38.

Figure 4:
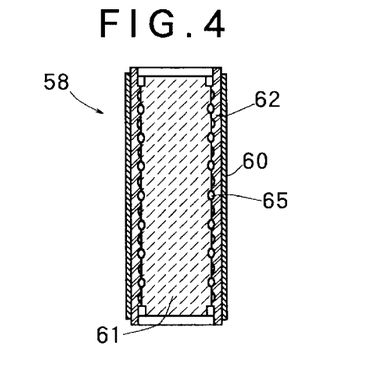
FIG. 4 is a sectional view showing one embodiment of a second mixer which is applied to the present invention.
Figure 5:
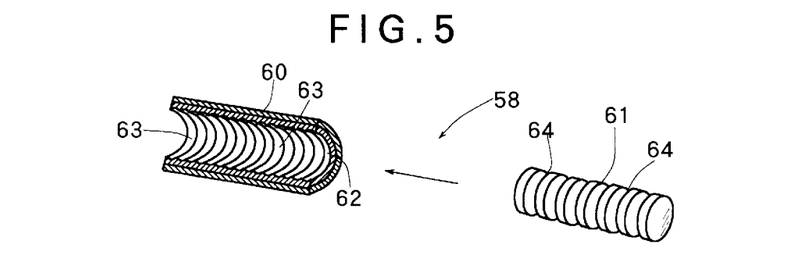
FIG. 5 is a perspective view showing the one embodiment of the second mixer which is applied to the present invention, with an outer sleeve cut into a half.

The second mixer 58 is of a circular sleeve-like configuration. The second mixer 58 comprises, as shown in FIGS. 4 and 5, an outer sleeve 60 made of metal, and an inner sleeve 61 made of metal or ceramic. A mixer tube 62 made of ceramic is integrally attached to inside the outer sleeve 60. A lead groove 63 is axially spirally formed in an inner surface of the mixer tube 62. The groove 63 is of a generally arcuate configuration in section. An arrangement pitch P of the spirally formed groove 63 is axially slightly reduced or increased.

In this case, the mixer tube 62 is preferably made of other hard synthetic resin, Teflon, or ceramic than metal because if an outer sleeve 19, an inner sleeve 61 and a mixer tube 62 made of metal should be used for analyzing a biological sample, the sample would be deposited on an inner surface of the mixer tube 62 and denatured.

The inner sleeve 61 is of a circular sleeve-like configuration. An outside diameter d of the inner sleeve 61 is smaller than an inside diameter D of the mixer tube 62. A small gap e to serve as a flow passage for an elute is formed between the inner sleeve 61 and the mixer tube 62. A lead groove 64 is axially spirally formed in a peripheral surface of the inner sleeve 61. The groove 64 is of a generally arcuate configuration in section. A width of the groove 64 is almost the same as that of the lead groove 63 and an arrangement pitch P of the spirally formed groove 64 is larger than the afore-mentioned arrangement pitch p. The spiral groove 64 is axially formed at generally equal pitches.

In this case, the arrangement pitch p of the lead groove 63 may be equally formed and the arrangement pitch P of the lead groove 64 may be axially slightly increased or reduced. By doing so, the lead groove 63 can more easily be formed compared with an irregular arrangement pitch.

Moreover, both the pitches p and P may be axially slightly increased or reduced. By doing so, a passage 65 for elute formed by the confronting lead grooves 63, 64 can be varied in sectional configuration and sectional area to enhance the mixing effect and efficiency.

In the above embodiment, the filter 57 and mixer 53 are spacedly interposed between the first mixer base 45 and the second mixer 58. However, it is preferred that they are arranged in as much proximal a relation as possible. By doing so, the mixer 26 can be designed small in size and light in weight, and in addition, the elutes 31, 32 mixed by the first mixer 45 can rapidly be fed to the second mixer 58.

The mixer for liquid chromatograph thus constructed comprises the first mixer 45 of a dynamic type and the second mixer 58 of a static type integral with the first mixer. Accordingly, the number of parts is reduced compared with a case where those mixers 45, 58 are separately situated. Moreover, the time and labor required for the mounting thereof are reduced and a mounting space is easily obtained, thus enabling them to be installed on the column oven.

The first mixer 45 includes a single mixing chamber 47 and its volume is designed to be as compact as possible. Accordingly, the mixer 45 can be designed small in size compared with as case where the mixer includes a plurality of mixing chambers. Moreover, a mixing of the liquid in a vertical direction to the flowing direction of the liquid as later described is enhanced to enhance followability to the gradient program.

A method for analyzing aldehydes contained in exhaust gas from automobiles in the analytical system of FIG. 1 and an operation thereof will now be described.

First, the switch valve 11 is operated have the dilution tube 3 communicated with the dilution liquid 9, and the cleaning tube 12 is closed.

Then, the three port valves 15, 17 are operated to have the liquid feed pump 10, the injector 16 and the mixer 18 communicated with one another. On the other hand, opposite ends of the bypass tube 19 are closed.

Then, the six port switch valve 2 is operated to have the port P1 communicated with the port P2, the port P3 with the port P4, and the port P5 with the port P6, respectively.

By doing so, the dilution tube 3 is communicated with the condensation tube 4 through the ports P1, P2, and the downstream side end portion of the condensation tube 4 is communicated with the discharge tube 7 through the ports P5, P6.

Further, the elution liquid conduits 27, 28 are communicated with the analytical tube 5 through the ports P4, P5, and further communicated with the drain through the detector 25.

When the liquid feed pump 10 is activated under such circumstances, the dilution liquid 9 in the dilution liquid container 8 is sucked up, then passed through the dilution tube 3 and fed to the injector 16. When a sample containing DNPH (2,4-dinitrophenyhydrazine) aldehydes contained in the exhaust gas is injected to it through the injector 16, the sample is mixed with the dilution liquid 9 and moved to the mixer 18 where the sample and the dilution liquid 9 are mixed. This liquid mixture flows into the six port valve 2.

The liquid mixture is moved to the condensation tube 4 via the port P1, port P2 of the six port valve 2 to condense specific gradients in the sample at the condensation column 23 and is accumulated. Thereafter, the liquid mixture is returned to the six port valve 2, moved to the discharge tube from the port P6 via the port P6, and then discharged.

On the other hand, on or about the condensation of the sample, the agitation motor 51, the liquid feed motor 51 and the liquid feed pumps 33, 34 are activated.

When the agitator 51 is activated, the rotor 52 is rotated to draw the agitator 50 within the mixing chamber 47 by its magnetic force so that the agitator 50 is drawn to the bottom portion of the mixing chamber 47 for synchronous rotation.

When the liquid feed pumps 33, 34 are activated, the elutes 31, 32 in the elute containers 29, 30 are sucked up and introduced into the elute tubes 27, 28. Then, the elutes 31, 32 are moved to the three-way joint 35 and converged from the inner inlet port 39 via the outlet port 41. Thereafter, they are moved from the passage 44 through the through-hole 48 and introduced into the mixing chamber 47 of the first mixer 45.

The elutes 31, 32 are forcibly agitated for mixture by the agitator 50, which is rotating in the mixing chamber 47, and then flow from the outlet port 49 to the recess 43.

In this case, because the mixing chamber 47 is small in volume and of a low dead volume, the elutes 31, 32 are rapidly mixed, thereby enhancing a vertical mixture to the flowing direction thereof, i.e., a mixture in which the mixing ratios of the two kinds of liquids are gradually varied.

Thereafter, a liquid mixture of the elutes 31, 32 is moved through the filter 57 so that foreign matter is removed therefrom. The liquid mixture is then moved through the introduction hole 56 and introduced to the second mixer 58.

In this case, because the introduction hole 56 is extremely reduced in diameter and small in size, the volume of the introduction hole 56 is suppressed to be as small as possible, thereby maintaining the mixing state of the liquid mixture moving therethrough so that the mixture will not be denatured.

In the second mixer 58, the liquid mixture of the elutes 31 and 32 is moved spirally around the inner periphery 61 along the passage 65 defined by the peripheral surface of the inner sleeve 61 or the lead groove 64. During the flowing process, the liquid mixture is caused to mix with a secondary stream i.e., a vertical flow to the flowing direction thereof, and thus the condensation gradient is maintained.

Figure 6:
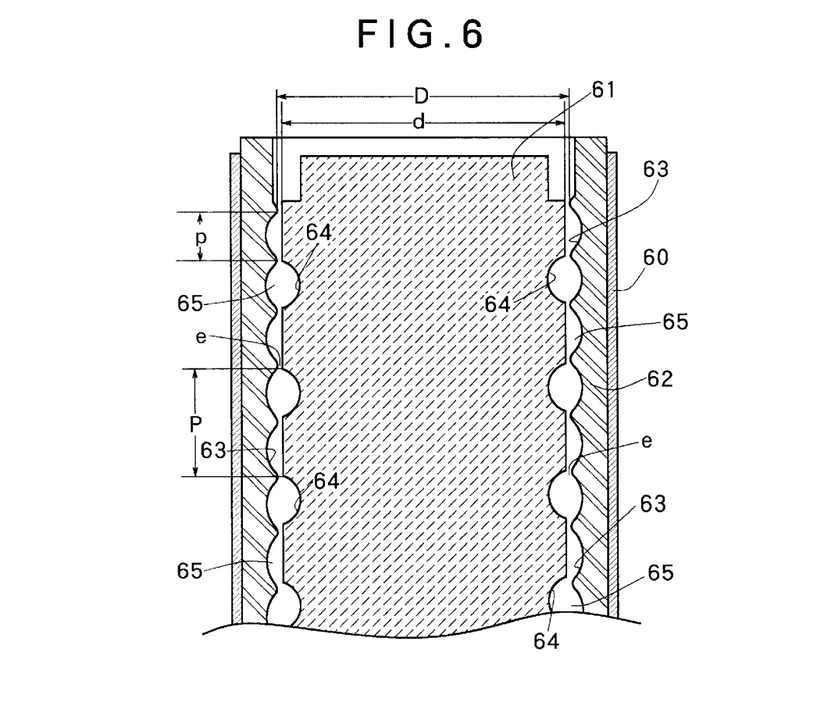
FIG. 6 is a partly enlarged sectional view of FIG. 4.

In this case, a plurality of passages 65 are formed in the periphery of the inner sleeve 61 as shown in FIG. 6 and have various sectional areas and sectional configurations as shown. The passages 65 are strictly changed in radius of curvature so that various actions of the secondary stream are set.

Accordingly, the liquid mixture of the elutes 31 and 32 are subjected to the mixing action for mixture over a long passage and moved while varying in flow rate, and the maintenance of the afore-mentioned condensation gradient is enhanced under the various effects of the secondary stream.

Moreover, a part of the elutes 31, 32 moving through the passage 65 slip through the gap e and flowed into an adjacent or separated other passage 65 where the flow rate of the elutes 31, 32 are uniformed to reduce the effect of pulsation.

The liquid mixture of the elutes 31, 32 is passed through the second mixer 58 with the condensation gradient maintained. After movement in the second mixer 26, the liquid mixture is introduced by the mixing tube 6 into the six port valve 2 and flows into the analytical tube 5 from the port P4 via the port P3. Then, it is discharged through the analytical column 5 and the detector 25.

Under such circumstances, when the intended gradients are all condensed by the condensation column 23, the six port switch is switched to have the port P1 communicated with the port P6, the port P2 with the Port P3, and the port P4 with the port P5, respectively.

By doing so, the dilution tube 3 is communicated with the discharge tube 7 through the ports P1, P6, while the mixing tube 6 is communicated with the condensation tube 4 through the ports P4, P5. The downstream side end portion of the condensation tube 4 is communicated with the analytical tube 5 through the ports P2, P3, and communicated with the drain by the detector 25.

As a consequence, the dilution liquid 9 is discharged via the dilution tube 3, the ports P1, P6 and the discharge tube 7. The liquid mixture of the elutes 31, 32 is introduced into the condensation tube 4 via the ports P4, P5 and, elutes the sample condensed and accumulated in the condensation column 23 so as to be sent out. The eluted sample is introduced from the condensation tube 4 into the analytical tube 24 via the ports P2, P3, and is separated by the analytical column 24 so that each ingredient is detected by the detector 25 one after another.

In this case, the elutes 31, 32 are filly and accurately mixed by the mixer 26 into a complete mixed state.

Because the elutes 31, 32 have the sample move with the condensation gradient maintained in the vertical direction to the flowing direction, the present invention is advantageously applied to the gradient elution in which samples are eluted while gradually varying the mobile phase compositions, and particularly advantageously applied to elution of samples containing multiple components.

In order to confirm the above, the inventor of the present invention used the mixer 26 of the present invention for mixing the elutes, and analysis experiments were repeated five times using the conventional static mixer, namely, a mixer formed of a coil spring like mixer tube with a plurality of beads filled therein under the same conditions. The results of FIGS. 7 and 8 were obtained.

Figure 7:
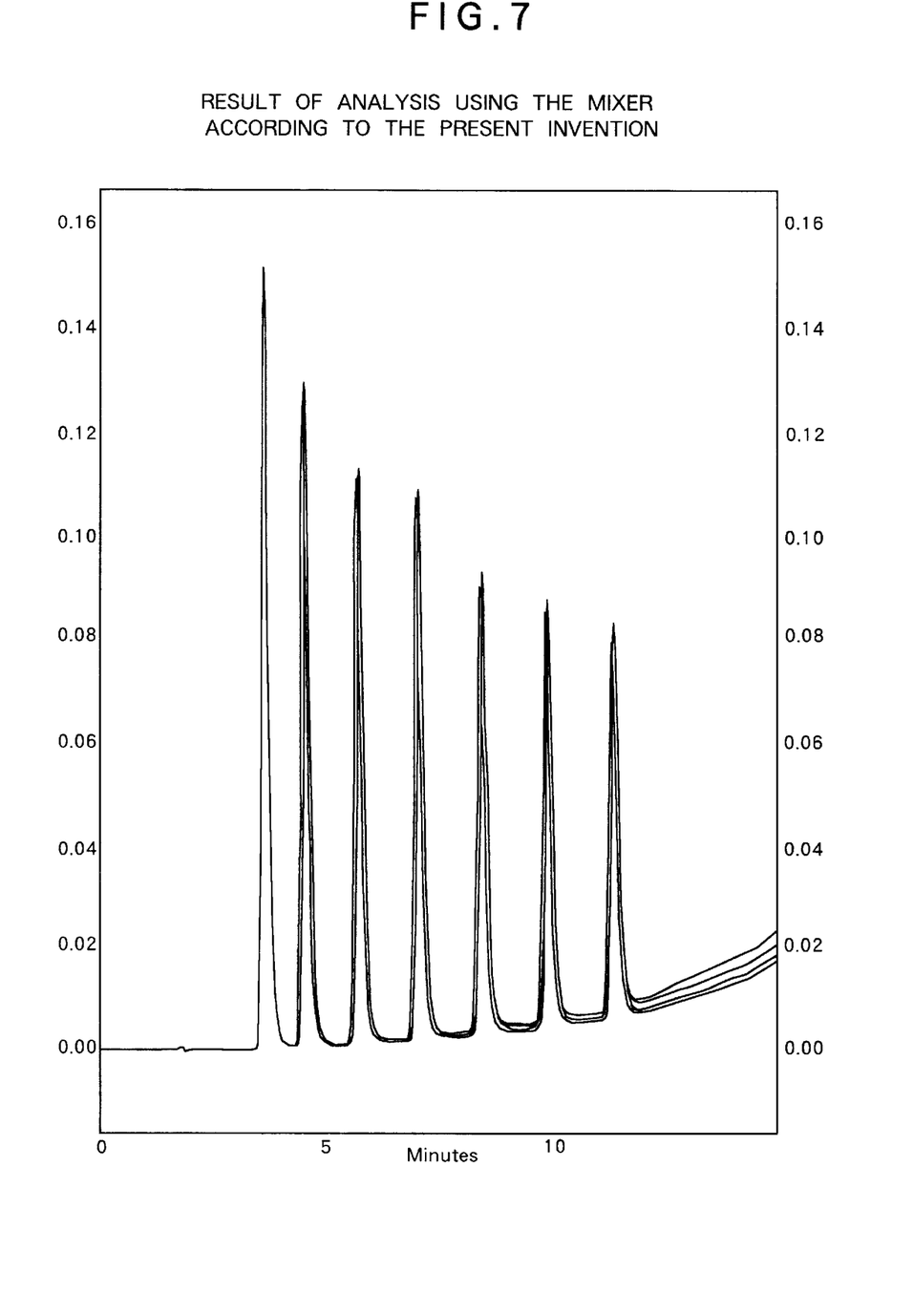
FIG. 7 is a graph of an experiment showing a result of analysis using a mixer of the present invention.
Figure 8:
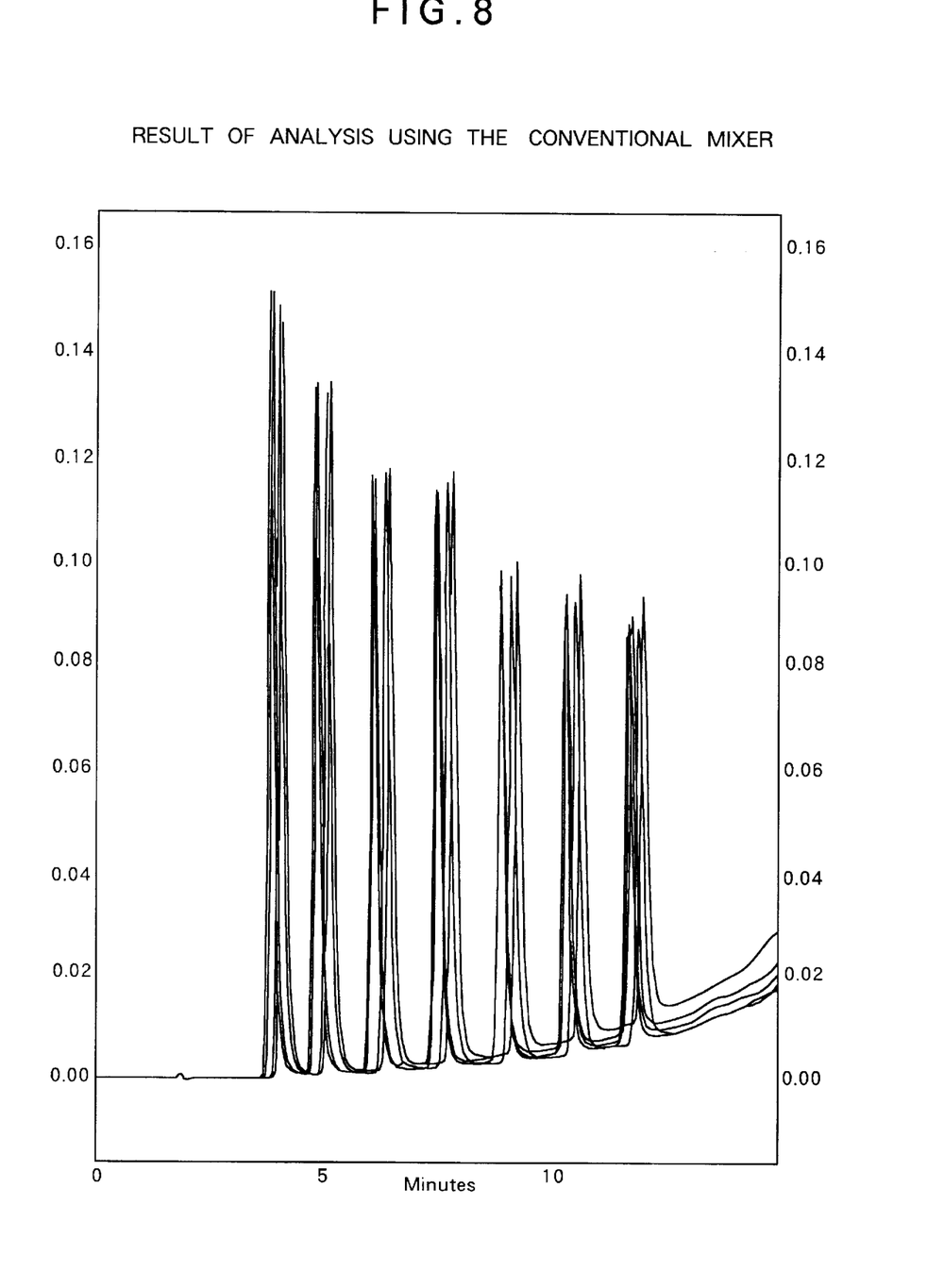
FIG. 8 is a graph of experiment showing a result of an analysis using a conventional mixer.

In the illustrations, the results of the analysis are shown in an overlapped manner.

Figure 9:
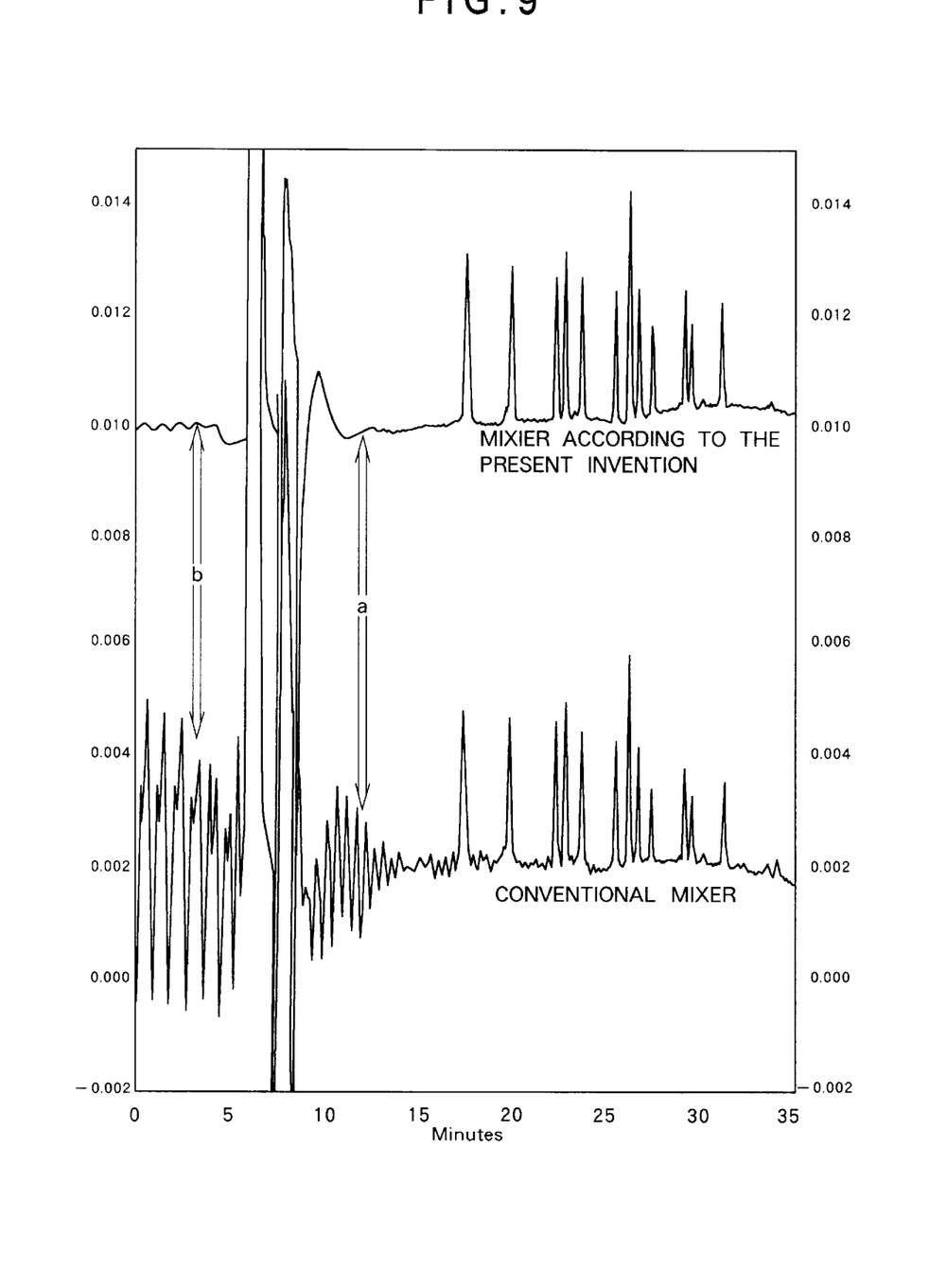
FIG. 9 is a graph of an experiment showing a comparison of the results of analysis using the mixer according to the present invention and the conventional mixer.

When the results of analysis obtained by using the mixer 26 of the present invention and by using only the conventional static mixer were compared, the result of FIG. 9 was obtained. FIG. 9 shows the results of the two in offset relation in the direction of the vertical axis.

FIG. 7 shows a result of experiment using the mixer 26 of the present invention. Five chromatographs of FIG. 7 are generally the same. It was confirmed that the gradient is performed very correctly and accurately.

On the other hand, FIG. 8 shows the result of analysis using only the conventional static mixer. It was confirmed that the chromatograph of FIG. 8 is large in irregularity and the gradient is low in correctness.

Further, in FIG. 9, a distinctly clear difference appears in noise and base line at the ports a, b. It was confirmed that the mixing is insufficient, many noises are generated, and the base line is unstable in the conventional example, while the noise is less, the base line is stable, and mixing is fully performed in the present invention.

Therefore, the mixing according to the present invention correctly and rapidly follows the gradient program for gradually increasing the solvent strength by varying the mobile phase compositions in the gradient elution, and enhance the elution of predetermined ingredients corresponding to the program, thereby smoothly separating them.

For this reason, troubles are obviated such that the retention time of the peak of each ingredient is correct and stable in the chromatogram and a plurality of ingredients are not separated but eluted simultaneously.

Actually, only a trace of the aldehydes as the samples is contained in the exhaust gas from automobiles, and there are many cases were no sample of a predetermined condensation can be obtained by the aforementioned condensation.

[In view of the above, there is actually employed a method in which a large quantity of sample is injected and a required quantity of sample is condensed for analysis.

In this case, the resistor setter 20 is operated to set the resistor tube 21 corresponding to a separation ratio between the dilution tube 3 and the bypass tube 19. In the embodiment, the flow rate of the bypass tube 19 is set to about three to four times the dilution tube 3.

When the liquid feed pump 10 is drive under such conditions, the dilution liquid 9 flows dividedly into the dilution tube 3 and the bypass tube 19, the sample is injected from the injector 16 into the dilution liquid 9 moving in the dilution tube 3, and the sample and the dilution liquid 9 divided into the bypass tube 19 are converged by the three port valve 17.

Accordingly, since the sample is diluted by a large quantity of the dilution liquid 9, it can easily be absorbed to the condensation column 23 by diluting the sample after the solvent is replaced by the dilution liquid 9 even in the case where the solvent dissolving the sample is large in strength.

Thereafter the dilution liquid 9, which has diluted the sample, is introduced into the mixer 18 where the sample and the dilution liquid 9 are fully mixed. Thereafter, the sample is condensed and accumulated in the condensation column 23.

In this case, because the sample and the dilution liquid 9 are fully mixed and the sample is uniform in condensation, the column filler of the condensation column 23 and the sample act in a stable manner so that the condensation efficiency of the sample is increased to ensure the condensation.

Thereafter, the six port valve 2 is switched so that the condensed sample in the condensation column 23 is eluted in the elutes 31, 32 and sent into the analytical tube 5 where the sample is separated in the analytical column 24.

After completion of analysis, the switch valve 11 is operated to have the cleaning tube 12 communicated with the cleaning liquid 14 and then the liquid feed pump 10 is activated.

By doing so, the cleaning liquid 14 is moved through the dilution tube 2 and the bypass tube 19 to clean the inside of the tubes, and further moved through the mixer 18, the condensation tube 4 and the condensation column 23 to clean an impurity temporarily adhered thereto, so that generation of a peak by the impurity is prevented and a reproduction of the next analysis is maintained.

The afore-mentioned cleaning is particularly important for the analysis of ingredients contained in exhaust gas from automobiles, which gas contains a large quantity of impurities.

Figure 10:
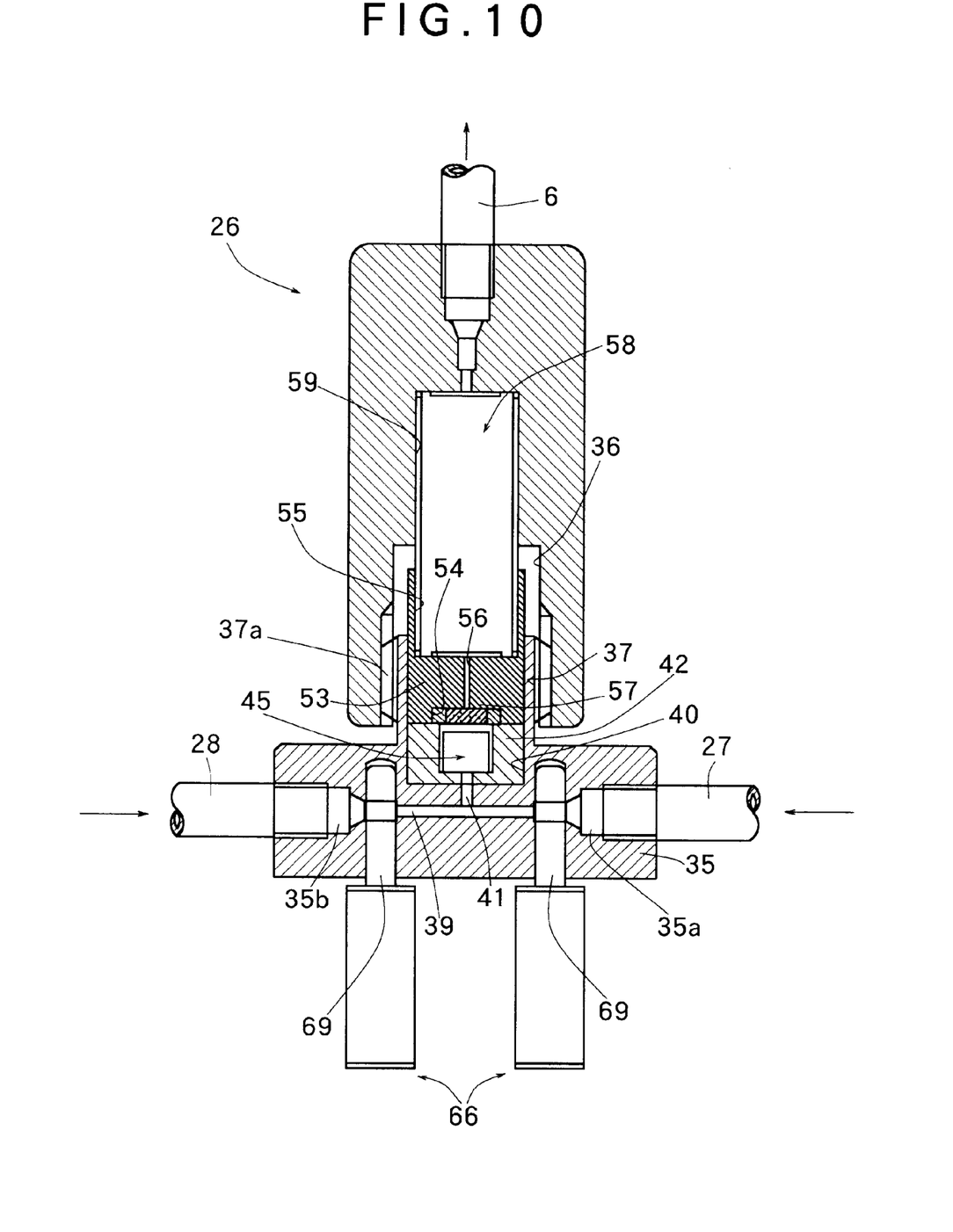
FIG. 10 is a sectional view showing another embodiment of the present invention.
Figure 11:
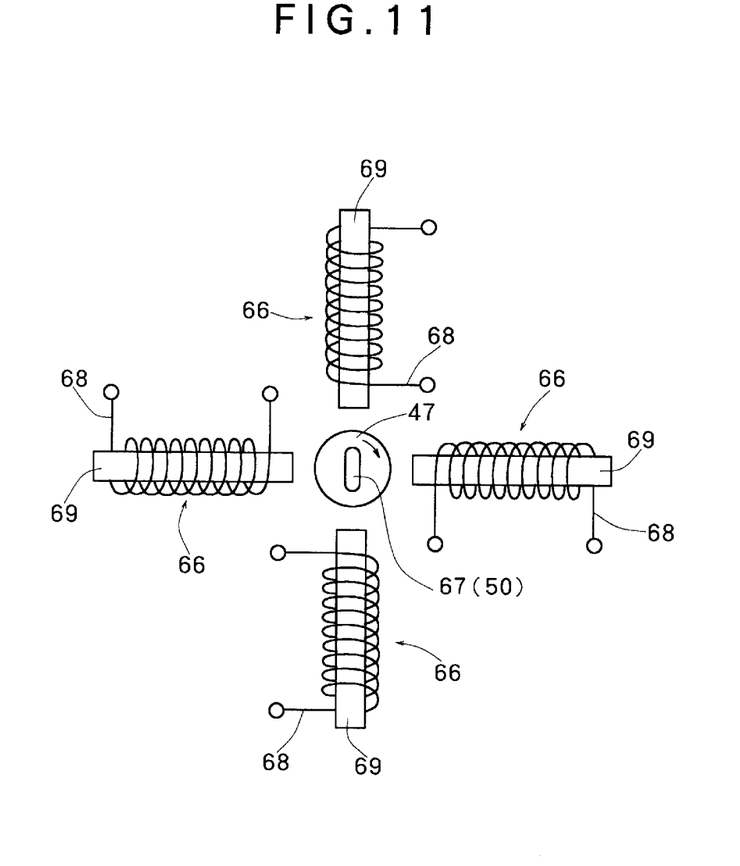
FIG. 11 is a plan view schematically showing a main part of the embodiment of FIG. 10.
Figure 12:
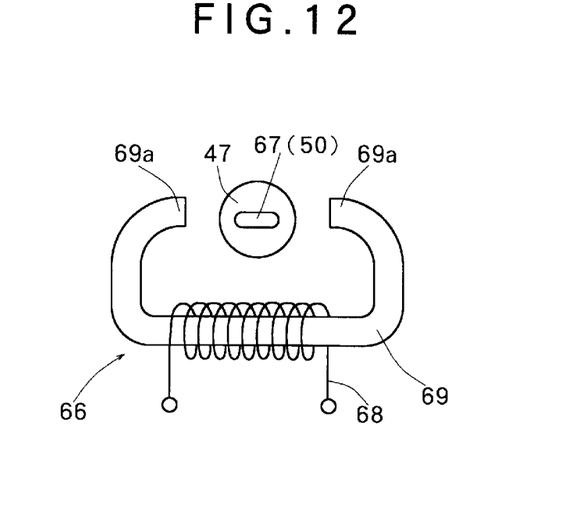
FIG. 12 is a plan view schematically showing one example of application of the embodiment of FIG. 10.

FIGS. 10 through 12 show another embodiment of the present invention, in which those parts corresponding to the construction of the previously-mentioned embodiment are denoted by identical reference numerals.

In this embodiment, a plurality of electromagnetic stones 66 (three or more in this embodiment) are arranged around a magnetic agitator 67 instead of the agitator 51 and the rotor 52, so that the supply of current to an electromagnetic coil of each electromagnetic stone 66 is controlled to rotate the magnetic agitator 67.

By doing so, there is no need of a provision of the agitation motor 51. Accordingly, the mixer can be designed smaller in size and lighter in weight to that extent.

In case a plurality of electromagnetic stones 66 are provided, if an iron core 69 of each electromagnetic stone 66 is bent in a generally C-shape such that opposite end portions 69a face each other with magnetic agitator 67 placed therebetween, the number of electromagnetic stones 66 can be reduced by half.

The features of the present invention are listed as follows.

According to a first aspect of the invention, a mixer for a liquid chromatograph for mixing plural kinds of liquids comprises a first mixer for forcibly agitating liquid, a second mixer for agitating liquid in accordance with a flow rate, a liquid passage for the first mixer and a liquid passage for the second mixer being in communication with each other, and the first and second mixers being integrally mounted. Owing to this feature, a sufficient mixing effect, as well as enhancement of mixing efficiency, can be obtained. In addition, the number of parts can be reduced and an installation space can be easily obtained. As a consequence, the mixer can be designed small in size and light in weight.

According to a second aspect of the invention, the first and second mixers are arranged in proximal relation. Owing to this feature, the liquid passage between the first and second mixers can be reduced in volume, and degradation of the mixing state can be prevented. In addition, the mixer can be designed to be small in size and light in weight.

According to a third aspect of the invention, the first mixer can perform selective agitation of liquid between forcible agitation and agitation in accordance with a flow rate. Owing to this feature, a single mixer can conveniently be used as both a so-called dynamic mixer and static mixer.

According to a fourth aspect of the invention, the first mixer is arranged in a liquid passage on an upstream side of the second mixer. Owing to this feature, liquids to be mixed can be forcibly mixed in the first place, thereby increasing the mixing efficiency.

According to a fifth aspect of the invention, the first mixer includes a mixing chamber in conmnunication with the liquid passages and an agitator rotatably received in the mixing chamber. Owing to this feature, the liquid can be forcibly mixed by rotation of the agitator.

According to a sixth aspect of the invention, the first mixer includes a single mixing chamber having a small volume and in communication with the liquid passages, and a single agitator. Owing to this feature, the mixer can be reduced in dead volume, and therefore the mixing effect in the mixer can be enhanced.

According to a seventh aspect of the invention, the agitator is variable in speed of rotation within a range from zero to a predetermined speed. Owing to this feature, various ways of use can be selected in accordance with the mixing conditions and the mixer can be used as a static mixer when the speed of rotation is zero.

According to an eight aspect of the invention, the second mixer includes an outer sleeve with a plurality of lead grooves spirally formed in an inner surface thereof, and an inner sleeve with a plurality of lead grooves formed in a peripheral surface thereof, the inner sleeve being dimensioned such that it can be inserted into the outer sleeve. Owing to this feature, there can be provided a versatile mixer which is small in size, light in weight and large in length.

According to a ninth aspect of the invention, a plurality of spiral passages having various sectional configurations and sectional areas are formed between the lead grooves in the outer sleeve and a peripheral surface and lead grooves in the inner sleeve. Owing to this feature, the mixing effect and mixing efficiency can be enhanced by moving the liquid to the various passages.

Specifically, the liquid can be moved to the spiral passage to enhance mixing of the liquid by secondary flow, so that a condensation gradient in the flowing direction can be maintained. As a consequence, mixing correctly following a mixing program can be obtained.

According to a tenth aspect of the invention, an outside diameter of the inner sleeve is smaller than an inside diameter of the outer sleeve, and a small gap is formed between the inner sleeve and the outer sleeve. Owing to this feature, there can be provided a liquid passage which is formed of a gap other than the lead groove.

According to an eleventh aspect of the invention, the small gap can communicate with the passage. Owing to this feature, pulsation of the liquid can be reduced and prevented.

According to a twelfth aspect of the invention, each pitch of the lead grooves of at least one of the outer and inner sleeves is axially gradually increased or decreased. Owing to this feature, a passage having various sectional configurations and various sectional areas can be formed.

According to a thirteenth aspect of the invention, the mixer for liquid chromatograph is a gradient mixer. Owing to this feature, the mixture as a gradient mixer, can correctly follow a mixing program while maintaining the concentration gradient which is varied with the passage of time.

According to a fourteenth aspect of the invention, the agitator is rotated by electromagnetic force of a rotor capable of rotating at a variable speed. Owing to this feature, the agitator can be rotated reliably and in a stable manner.

According to a fifteenth aspect of the invention, a plurality of electromagnetic stones are arranged around the agitator and the agitator can be rotated at a variable speed by controlling the supply of current to an electromagnetic coil of each of the electromagnetic stones. Owing to this feature, since the rotor is not rotated by a motor or the like, the generation of noise and vibration can be prevented, and in addition, the mixer can be designed to be small in size and light in weight.

What is claimed is:

1. A mixer for a liquid chromatograph for mixing plural kinds of liquids, comprising:

a first mixer for forcibly agitating liquid, said first mixer being provided within a joint that is connectable with a plurality of elute tubes;

a second mixer for agitating liquid in accordance with the flow rate of the liquid, said second mixer comprising an outer sleeve having a spirally formed lead groove in an inner peripheral surface thereof and an inner sleeve having a lead groove spirally formed in a peripheral outer surface thereof, said inner sleeve being dimensioned such that it can be inserted into said outer sleeve, and said second mixer being provided within a cap that is connectable with a mixing tube;

wherein said joint and said cap are integrally and removably joined with one another by a threaded engagement; and a liquid passage communicating said first mixer with said second mixer.

2. The mixer of claim 1, wherein a spiral passage having various sectional configurations and sectional areas is formed between said lead groove in said outer sleeve, and said peripheral outer surface and said lead groove of said inner sleeve.

3. The mixer of claim 1, wherein the pitch of at least one of said lead groove of said outer sleeve and said lead groove of said inner sleeve axially gradually changes.

4. The mixer of claim 1, wherein said second mixer is on a mixer base having an introduction hole extending therethrough, said liquid passage comprising said introduction hole, and said introduction hole communicating with said first mixer.

5. The mixer of claim 4, wherein said mixer base is received in said joint adjacent to said first mixer.

6. The mixer of claim 1, wherein said first mixer comprises a mixing chamber and an agitator in said mixing chamber.

* * * * *